United States Patent [19]
Lee

[11] Patent Number: 6,161,549
[45] Date of Patent: Dec. 19, 2000

[54] ASH TRAY

[76] Inventor: Kyung Pyo Lee, 206-510 Old Hyundai APT, Apgujung-dong Kangnam-gu, Seoul, Rep. of Korea

[21] Appl. No.: 09/166,740

[22] Filed: Oct. 5, 1998

[30] Foreign Application Priority Data

Nov. 5, 1997 [KR] Rep. of Korea ................. 97-31052

[51] Int. Cl.[7] .................................................. A24F 15/08
[52] U.S. Cl. ...................... 131/231; 131/235.1; 131/242; 206/246
[58] Field of Search .................... 206/246; 55/385.8; 131/231, 235.1, 237.5, 238, 335, 344, 242, 242.6; 239/55, 56, 57, 60

[56] References Cited

U.S. PATENT DOCUMENTS

| | | | |
|---|---|---|---|
| 4,161,181 | 7/1979 | Nicks et al. ............... | 131/231 |
| 4,643,204 | 2/1987 | Ford ........................... | 131/231 |
| 4,732,591 | 3/1988 | Tujisawa et al. .......... | 55/279 |
| 4,780,370 | 10/1988 | Pointier ..................... | 428/404 |

*Primary Examiner*—Stanley S. Silverman
*Assistant Examiner*—Robert McBride
*Attorney, Agent, or Firm*—Nathan N. Kallman

[57] ABSTRACT

The present invention relates to an ash tray, and more particularly to an ash tray which can sanitarily control as well as automatically extinguish a smoking cigarette butt when it is put in the ash tray. In accordance with the present invention, the ash tray comprises a tube body in which cigarette butts are received and a porous member is equipped to the inward lower; a cap covering the upper end of the tube body; and an aroma tube coupled to the lower of the tube body in which an aromatic is equipped therein.

3 Claims, 4 Drawing Sheets

ASH TRAY

BACKGROUND OF THE INVENTION

1. Field of the Invention

The present invention relates to an ash tray, and more particularly to an ash tray which can sanitarily control as well as automatically extinguish a smoking cigarette butt when it is put in the ash tray.

2. Description of the Prior Art

The ash tray is used to put and keep cigarette butts or cigarette ashes therein. The conventional ash tray has a protrusion 20 which is protruded in the up direction in order to be extinguished by rubbing the lighted cigarette on the center of a container 10 in which cigarette butts or cigarette ashes are received as shown in FIG. 1.

However, such an ash tray was complicated and inconvenient because the lighted cigarette was rubbed on the protrusion extinguish it. In the case of extinguishing the light of a cigarette as above, the light of a cigarette is sparked on the outside of the container. Further, in the case of leaving the light of a cigarette thoroughly not extinguished, it can cause a fire In addition, in the case of touching the container due to carelessness, cigarette butts or cigarette ashes filled in the container may be scattered.

SUMMARY OF THE INVENTION

Therefore, an object of the invention is to solve the above-mentioned problems involved in the conventional ash tray and to provide an ash tray which can sanitarily control and easily extinguish the light of a cigarette.

In accordance with one aspect, the present invention provides an ash tray comprising: a tube body in which cigarette butts are received and a porous member that; a cap covering an upper end of said tube body; and an aroma tube disposed at a lower portion of the tube body in which an aromatic is provided.

BRIEF DESCRIPTION OF THE DRAWINGS

Other objects and aspects of the invention will become apparent from the following description of embodiments with reference to the accompanying drawings in which.

DETAILED DESCRIPTION OF THE PREFERRED EMBODIMENTS

Figure 1:
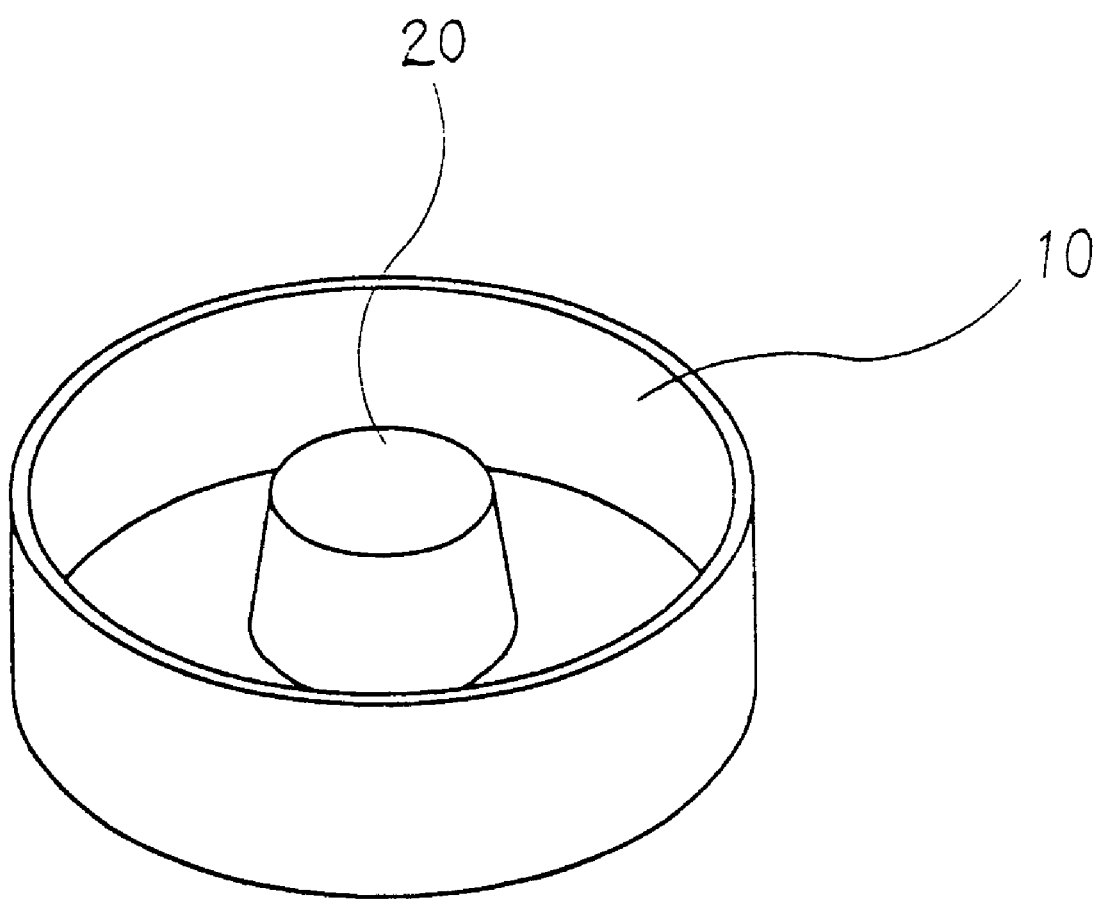
FIG. 1 is a perspective view showing an embodiment of a conventional ash tray.
Figure 2:
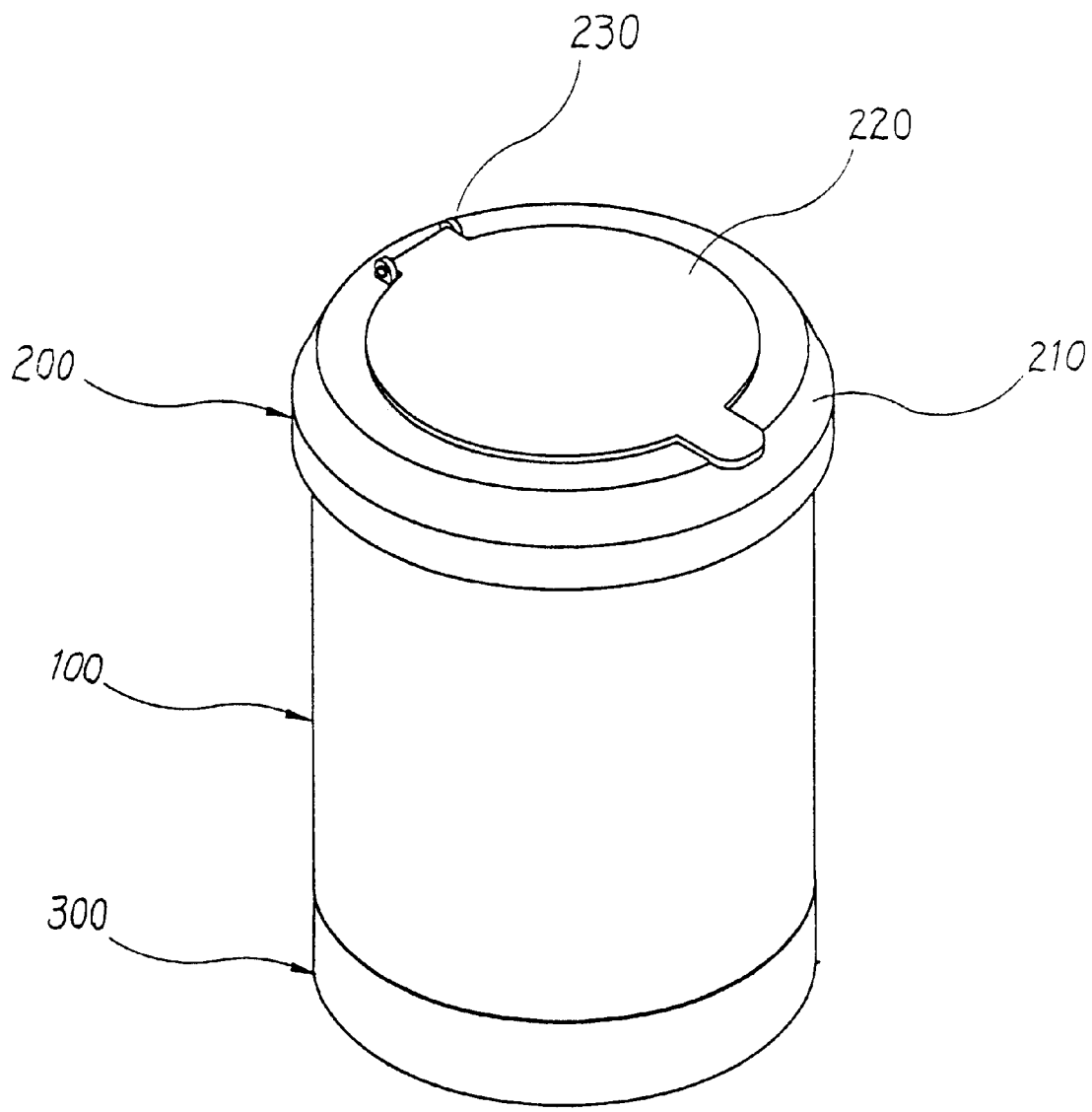
FIG. 2 is a perspective elevation view showing an embodiment of the present invention.
Figure 3:
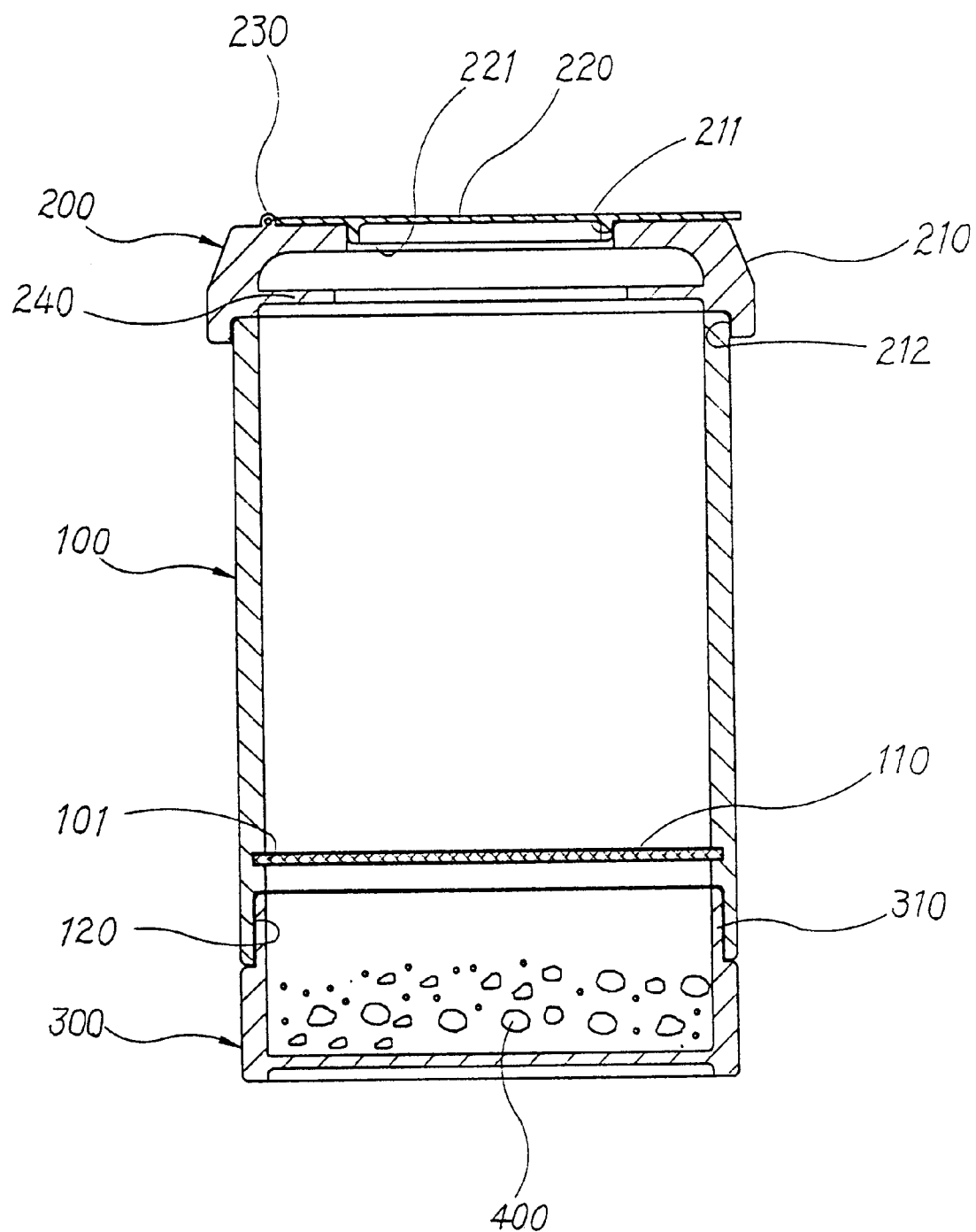
FIG. 3 is a side sectional view showing an embodiment of the present invention.

In accordance with the present invention and as shown in FIGS. 2 and 3, the ash tray includes a tube body 100 in which cigarette butts are received, a cap 200 covering an upper opening portion of the tube body 100, and an aroma tube 300 coupled to a lower end of the tube body 100 in which an aromatic 400 such as a sponge including moisture, or other perfume is stored as shown in FIG. 3.

The tube body 100 includes a porous member 110 having a mesh structure on which cigarette butts are deposited through which the aromatic aroma is passed. The porous member is inserted and fixed in a fixed groove 101, and a coupling groove 120 in the lower end portion of the tube body 100.

The section of the tube body 100 can be the polygonal form as well as circular form. The tube body 100 is composed of an upper tube body portion 130 of which a top end is coupled to the cap 200, and a lower tube body 140 at the lower end of the upper tube body portion 130 to which the porous member 110 is coupled therein. As a result, the porous member 110 can be replaced by separating the tube body portion and porous member as shown in FIG. 4.

The cap 200 coupled to the top end of the tube body 100 is composed of a cap main body 210 to which an inserting hole 211 from the outer of the tube body 100 to the inner thereof is formed. A cover 220 is coupled to a side of the top end of the cap main body 210 by means of a hinge 230 to cover the inserting hole 211 the central portion thereof. Smoking exhaust protection jaws 240 are formed on an inner circumferential surface of the cap main body in series at a constant distance so that the smoke is not exhausted to the outside of the tube body by swirling the smoke to the down direction when the cigarette butts disposed on the inner circumferential surface thereof are put in the tube body 100. A coupling groove 212 to which the top end of the tube body 100 is closely adhered and coupled is formed on the bottom end of the cap main body. The cover 220 has a protrusion 221 inserted in the inserting hole 211 of the cap main body 210 the bottom surface thereof. In addition, the tube body 100 and the cap main body 210 can be formed to be spirally coupled by forming a male screw and a female screw respectively on the portions contacting each other.

The aroma tube 300 of a cylindrical form, sealed to the lower end, which comprises a coupling rib 310 so to be coupled to a coupling groove 120 formed at the lower end of the tube body 100 the upper end thereof, not only stores the aromatic for removing a bad smell but also collects minute cigarette ashes filtered through the porus member 110 of the tube body. The tube body 100 and the aroma tube 300 can be formed to be spirally coupled by forming a male screw and a female screw respectively on the portions contacting each other.

Figure 4:
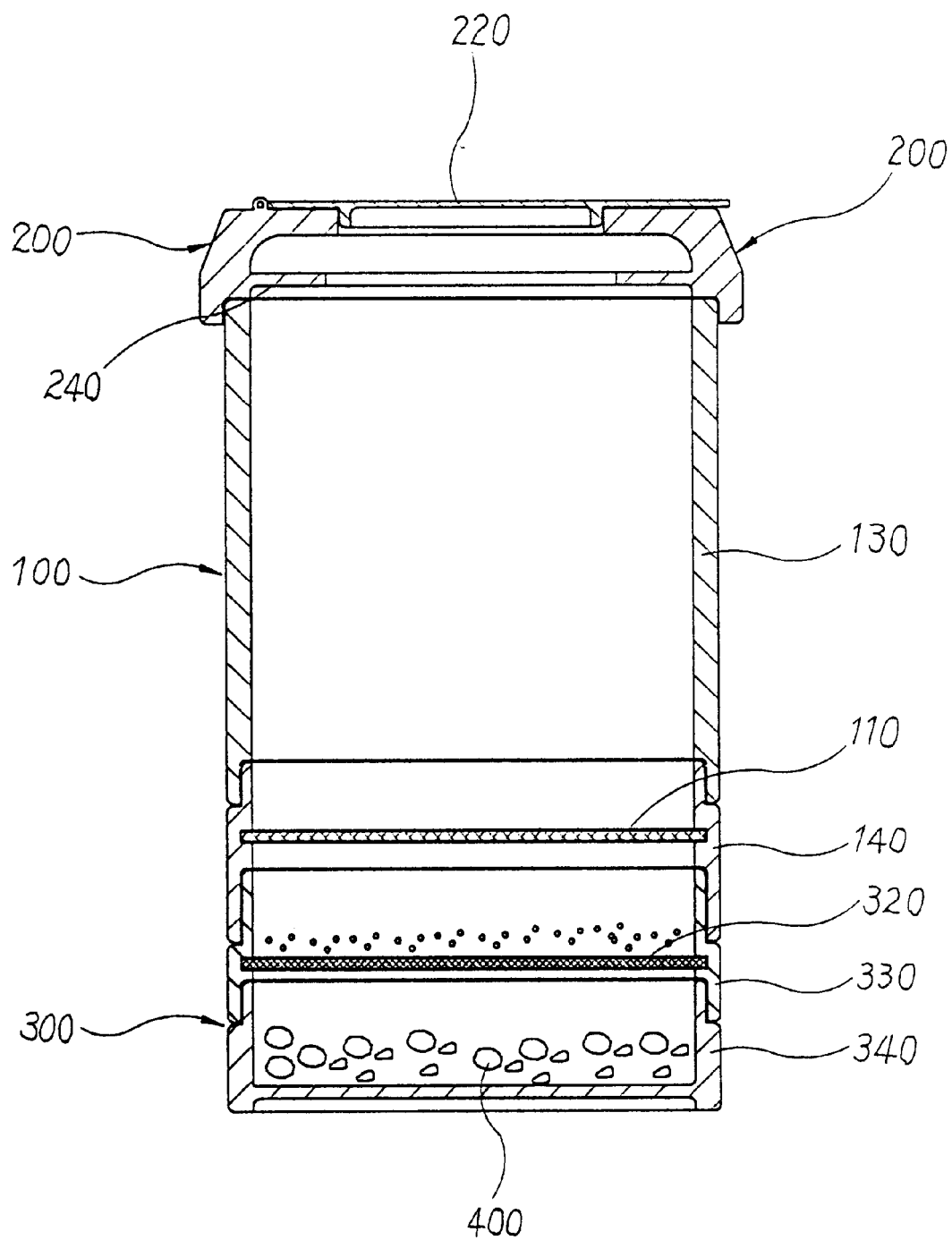
FIG. 4 is a side sectional view showing another embodiment of the present invention.

The aroma tube 300 is according to the sectional form, coupled to the lower end of the tube body 100 as shown in FIG. 4. The tube body is composed of a top aroma tube 330 having a porous member 320 of a mesh structure equal to or smaller than the porus member 110 coupled to the tube body 100, and a bottom aroma tube 340 which is sealed being coupled to the lower end of the top aroma tube 330. As a result, an aromatic 400 stored in the aroma tube 300 is easily replaced being coupled and separated to each other, and the aromatic 400 and cigarette ashes are prevented from mixing.

The operation of the ash tray of the present invention constructed as above is as follows. If a smoking cigarette butt is put in the tube body upon opening the cover 220 of the cap 200 and then the tube body 100 is sealed upon closing the cover 220, the light of the smoking cigarette is extinguished by burning down oxygen, in the tube body 100 after the cigarette butt is burnt in the tube body. Further, the aromatic 400 stored in the aroma tube removes the constant bad smell produced from the cigarette butts contained in the tube body through the porous member 110 of the tube body by mixing the bad smell and the aroma.

As described above, the ash tray of the present invention is composed of the tube body having the porous member on which cigarette butts are hung, the cap sealing the upper end of the tube body, and the aroma tube storing the aromatic by forming to be coupled and separated to each other, which can prohibit the aromatic from producing the bad smell from the cigarette butts, and control after separating and collecting the cigarette butts and ashes. This results in better sanitary environment.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. An integral ash tray assembly for receiving and extinguishing smoking cigarette butts comprising:

a hollow tube body having an upper end portion and a lower end portion;

a cap assembly disposed over said upper end portion including an inserting hole for receiving cigarette butts and a hinged cover for covering said inserting hole and for exposing said inserting hole to receive a cigarette butt;

an aroma tube containing an aromatic material coupled to the lower portion of said tube body; and a removable and replaceable first porous member formed of a mesh material on which cigarette butts are deposited, wherein said first porous member is located above said aroma tube through which aroma from said aroma tube passes a second aroma tube and a second porous member disposed above said first aroma tube and below said first porous member, wherein said second porous member has a mesh with a mesh structure equal to or smaller than that of said first porous member;

said integral ash tray being closed and sealed when said hinged cover is closed so that no smoke is exhausted from said ash tray assembly to the ambient environment.

2. The ash assembly tray according to claim 1, wherein a smoking exhaust protective jaw is formed with said cap assembly.

3. An ash tray assembly as in claim 1, wherein said aromatic material comprises a moist sponge or a perfume.

* * * * *